United States Patent [19]

Keyes et al.

[11] 4,393,659
[45] Jul. 19, 1983

[54] METHOD AND APPARATUS FOR PRODUCING STERILE SLUSH ICE

[75] Inventors: Richard M. Keyes, Lake Summerset; Stephen W. Schwitters, Rockford, both of Ill.

[73] Assignee: Taylor Freezer Company, Rockton, Ill.

[21] Appl. No.: 384,014

[22] Filed: Jun. 1, 1982

[51] Int. Cl.³ .............................................. F25C 1/00
[52] U.S. Cl. ............................................ 62/66; 62/78; 62/342; 62/353; 62/434; 312/236; 422/99
[58] Field of Search ............... 422/99; 62/59, 78, 340, 62/342, 344, 353, 356, 434, 66; 312/214, 236

[56] References Cited

U.S. PATENT DOCUMENTS

| | | | |
|---|---|---|---|
| 2,072,347 | 3/1937 | Strebler | 62/59 |
| 2,082,756 | 6/1937 | Pridham | 62/434 |
| 3,318,105 | 5/1967 | Burroughs et al. | 62/66 |
| 3,402,567 | 9/1968 | Menzel | 62/306 |
| 3,456,577 | 7/1969 | Menzel | 99/247 |
| 3,811,494 | 5/1974 | Menzel | 62/342 |
| 3,930,535 | 1/1976 | Menzel | 62/342 |

Primary Examiner—Ronald C. Capossela
Attorney, Agent, or Firm—Vernon J. Pillote

[57] ABSTRACT

A method and refrigeration apparatus for producing a sterile slush ice from a sterile liquid for use in surgical procedures. The refrigeration apparatus includes a cabinet having a heat transfer basin at the top and refrigeration mechanism in the cabinet for cooling the heat transfer basin. A separate sterile product basin is positioned in the heat transfer basin and cooled through a heat transfer medium in the product basin. A sterile liquid is deposited in the product basin and ice is scraped off the walls of the product basin with a sterile scraper. A sterile cover including a liquid impervious cover sheet is provided for covering the heat transfer basin and the heat exchange medium therein and the upper portion of the refrigeration apparatus.

8 Claims, 4 Drawing Figures

U.S. Patent   Jul. 19, 1983   4,393,659
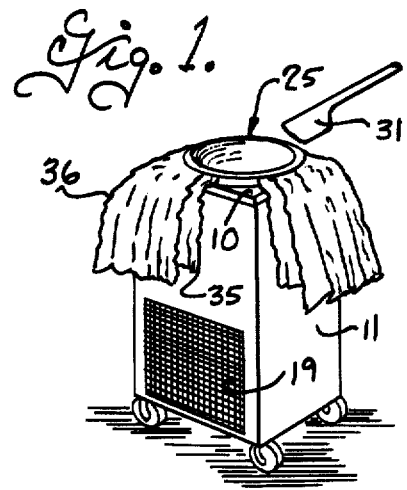
Fig. 1.
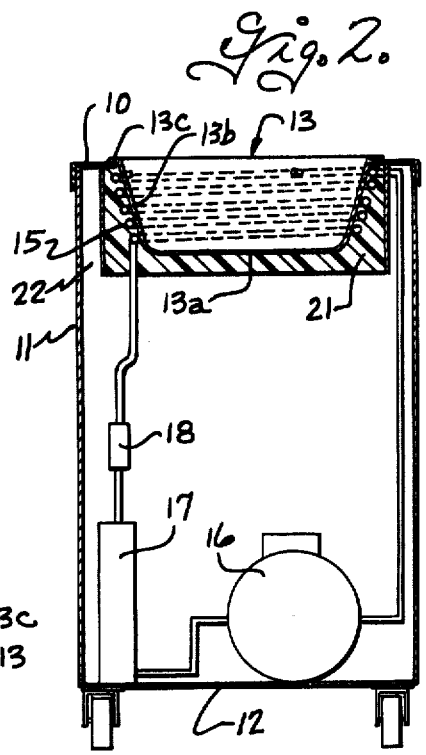
Fig. 2.
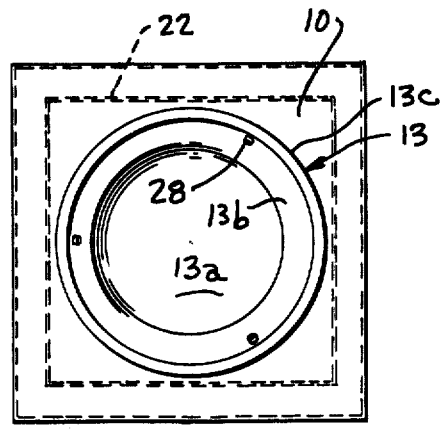
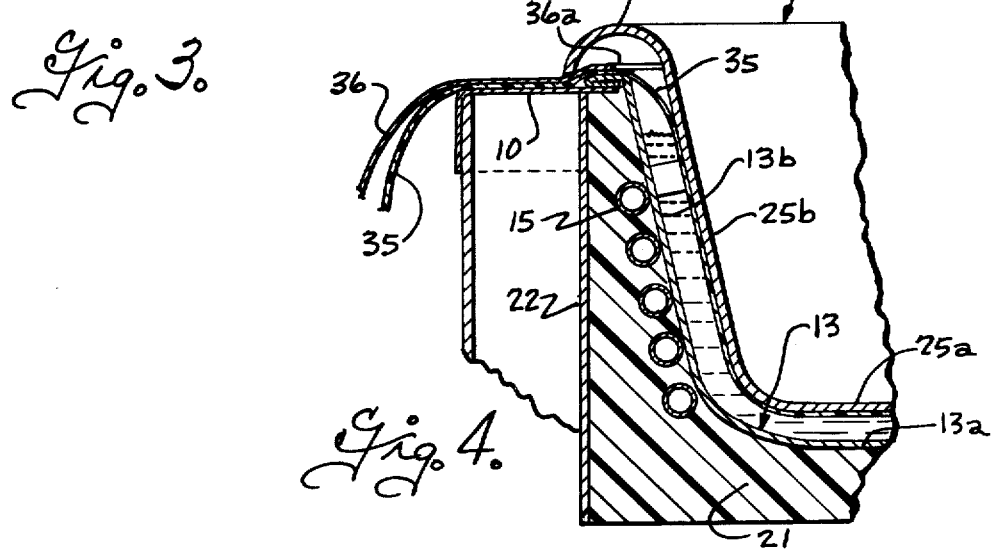
Fig. 3.
Fig. 4.

METHOD AND APPARATUS FOR PRODUCING STERILE SLUSH ICE

BACKGROUND OF THE INVENTION

Some surgical procedures have been developed in which ice is utilized to reduce the temperature of certain organs or parts of the body during surgery. For example, in performing certain operations such as a nephrolithotomy, it has been found highly advantageous to pack finely divided ice in the wound around the kidney, after opening of the body cavity and from time-to-time during the operation. However, as with all instruments or materials that may come in contact with a wound during surgery, the ice used in such surgical procedures must be highly sterile, herein referred to as surgical sterile, and the production of surgical sterile ice has presented some problems. It has heretofore been the practice to produce the sterile ice required for surgery by providing a sterile liquid in a sealed flexible plastic bag and refrigerating the bag in a freezer until the liquid is a solid mass. When sterile ice is required for an operation, the bag with its frozen liquid contents is removed from the freezer and the bag then pounded with an implement to break up the ice mass, after which the bag is opened to discharge the crushed ice contents into a sterilized receptacle from which the crushed ice is removed for use during the operation. Crushing of the ice in a closed bag with an implement is not only cumbersome and laborious, but also frequently results in a rupturing of the bag. Rupturing of the bag during pounding on the bag to break-up the ice, destroys the sterility of the ice contents in the bag and effectively precludes the use of the ice in that bag in a surgical procedure. Further, it is difficult to obtain uniform finely divided ice by pounding on the frozen ice mass while it is in a sealed bag.

It has heretofore been proposed for example as shown in U.S. Pat. Nos. 3,402,567; 3,456,577; 3,811,494 and 3,930,535, to make soft ice machines with some provision for sanitizing the machines to some degree with chemicals and/or heat. However, such machines are not adapted to be sterilized to the high degree required to provide a surgical sterile ice product suitable for use in surgery. The freezing cylinders in these machines are formed as an integral part of the cabinet and refrigeration mechanism of the machine, and it is not possible to position the freezing cylinders of such machines in an autoclave or to otherwise heat such freezing cylinders to the temperatures and for the times required to obtain the high degree of sterility required to produce a surgical sterile ice. Further, the ice removers in these machines are driven by shafts that extend through a wall of the freezing cylinder and this not only aggravates the problem of sterilizing the machine to the degree required for surgical use but also presents a possible source of contamination of the ice product.

SUMMARY OF THE INVENTION

It is an object of this invention to provide a method and refrigeration apparatus for producing surgical sterile slush ice from a surgical sterile liquid for use in surgical procedures.

Another object of this invention is to provide a method and refrigeration apparatus for producing a surgical sterile slush ice, and which produces a finely divided slush ice product.

A more particular object of this invention is to provide a method and refrigeration apparatus for producing a surgical sterile slush ice for use in surgical procedures, in which all parts of the apparatus that come into contact with the sterile liquid or ice product produced therefrom, can be removed from the refrigeration apparatus for sterilization.

Accordingly, the present invention provides a method and refrigeration apparatus for producing a surgical sterile slush ice from a surgical sterile liquid for use in surgical procedures in which the refrigeration apparatus includes a cabinet having a heat transfer basin at the top and depending side walls defining an enclosure, a refrigeration mechanism in the cabinet including an evaporator in heat exchange relation to the heat transfer basin, and a compressor, condenser, and refrigeration expansion control means connected in a closed refrigeration loop with the evaporator and operable to cool the heat transfer basin to a temperature substantially below the freezing point of the sterile liquid. A separate sterilizable product basin dimensioned to be removably receivable in the heat transfer basin, is sterilized to surgical sterility and removably positioned and supported in the heat transfer basin, and a quantity of non-toxic heat transfer medium is provided into the heat transfer basin for transferring heat from the product basin to the heat transfer basin. A quantity of a surgical sterile liquid is introduced into the product basin, and the refrigeration apparatus is operated to cause congealing of the surgical sterile liquid on the walls of the product basin. A scraping tool sterilized to surgical sterility, is utilized to scrape ice off the walls of the product basin as the sterile liquid congeals thereon to produce a loose sterile ice slush in the product basin. A quantity of loose ice slush is allowed to accumulate in the product basin and is then removed from the product basin for immediate use in the surgical procedure. A separate sterile cover is provided for covering the top and upper portions of the cabinet to prevent operator contact with the upper portion of the cabinet during use of the apparatus. The separate sterile cover preferably includes a liquid impervious sheet that covers the heat transfer basin and the heat transfer medium therein.

These, together with other objects, features and advantages of this invention will be more readily understood from the following detailed description, taken in connection with the accompanying drawings wherein:

FIG. 1 is a perspective view of the apparatus for producing a surgical sterile slush ice;

FIG. 2 is a vertical sectional view through the apparatus of FIG. 1;

FIG. 3 is a top plan view of the apparatus; and

FIG. 4 is a fragmentary vertical sectional view illustrating parts of the apparatus on a larger scale.

The present invention relates to a method and apparatus for producing a surgical sterile slush ice from a surgical sterile liquid for use in surgical procedures. The surgical sterile liquid is of a type suitable for subcutaneous administration and is preferably approximately isotonic and may, for example, be a normal (0.85–0.9%) sodium chloride solution. Liquids suitable for subcutaneous administration are commonly used and readily available in hospitals and are commonly packaged in small rigid or flexible sealed containers of one half liter to one liter in size. Such fluids are packaged under sterile conditions and sterilized either before or after packaging.

A special refrigeration apparatus is provided for freezing the sterile liquid to produce the sterile slush ice. The refrigeration apparatus includes a cabinet having a top wall 10 and depending side walls 11 and a bottom 12 defining an enclosure, and an open top heat transfer basin 13 recessed in the top wall 10. As shown, the heat transfer basin 13 is disposed in an opening in the top wall and includes a generally flat bottom wall 13a, upwardly diverging side walls 13b and an outwardly directed flange 13c at the upper edge of the side walls that overlies and is rigidly secured to top wall 10 of the cabinet around the opening therein. A refrigerating mechanism is provided inside the cabinet and includes an evaporator 15 disposed in heat transfer relation to the heat transfer basin, a compressor 16, a condenser 17, and a refrigerant expansion control 18 connected in a closed refrigeration loop with the evaporator. Air vent openings 19, protected by louvers or a grille, are provided in the lower portion of the side walls 11 of the cabinet, to allow air circulation past the condenser and compressor. The condenser 17 can be of the static type or can have a fan for forcing cooling air thereover. The evaporator is herein shown in the form of a plurality of coils disposed around the outside of the side walls 13b of the heat transfer basin and preferably soldered or brazed thereto to improve the heat transfer between the evaporator coils and the basin. A thermal insulation 21, such as heat insulating foam or the like, is disposed around the evaporator coil and around the bottom and outer side walls of the heat transfer basin 13 to inhibit condensation or freezing of fluid on the outer side of the basin. In the embodiment illustrated, a metal shield 22 is secured at the top wall 10 of the enclosure and the insulation 21 is conveniently formed by pouring a settable foam insulating material into the space between the shield and the outer walls of the basin, when the basin is in an inverted position. The refrigerating apparatus is arranged to refrigerate the heat exchange basin to a temperature substantially below the freezing temperature of the liquid to be used in forming the sterile slush ice and preferably to a temperature of the order of 25° to 28° F. The refrigerant expansion control 18 is conveniently a conventional mechanical refrigerant expansion control or a capillary tube, and the refrigeration apparatus can be operated in continuous fashion when the compressor drive motor is energized for production of the slush ice product. If desired, the refrigerant expansion control can be of the type which is operated in response to the temperature of the heat exchange basin 13 to control the flow of refrigerant to the evaporator in a manner to maintain the temperature at the heat exchange basin a preselected value below the freezing temperature of the sterile liquid.

The refrigerating unit including the cabinet and heat exchange basin as thus far described, are not adapted to be sterilized to the high degree required for instruments and/or materials that directly or indirectly may come in contact with a wound during surgical procedures. In general, sterilization for surgical procedures is effected by either autoclaving, dry heat, or by gas sterilization. In autoclaving, the articles to be sterilized are subjected to saturated steam at elevated pressures and relatively high temperatures for substantial periods of time, for example, steam at a pressure of 750 mm. above atmospheric, at a temperature of 120° C. for fifteen minutes or more. Dry heat sterilization is utilized to sterilize articles which would be spoiled by moist heat or which are more conveniently kept dry. In dry heat sterilization, the articles are subjected to somewhat higher temperatures and for somewhat longer times than those used in autoclaving, for example temperatures of 170° C. for an hour or more. Gas sterilization is used for sterilizing heat sensitive material and utilizes liquids and gaseous ethylene oxide as a sterilizing agent. Gas sterilization is normally carried out in a pressure vessel or gas autoclave at slightly elevated temperature and pressure, for example temperatures of the order of 55° C. and pressures of 410 mm. above atmosphere for a period of an hour or more. The refrigerating unit thus far described including the heat exchange basin, cabinet, and refrigeration apparatus is not adapted for sterilization either by autoclaving, dry heat or gas sterilization since it is not only too large to fit in most autoclaves, but is also not suited to exposure to the high temperatures or moisture required for sterilization.

In accordance with the present invention, a separate sterilizable product basin 25 is provided and is dimensioned to be removably receivable in the heat transfer basin. The product basin 25 is made of a non-corrosive heat conducting material, for example stainless steel, which can withstand the temperatures involved in sterilization. The product basin is preferably contoured complementary to the heat transfer basin 13 and includes a generally flat bottom wall 25a, upwardly and outwardly inclined side walls 25b and a rim 25c at its upper edge adapted to extend over the top of the rim on the heat transfer basin. A means such as spacers 28 are advantageously provided on the heat transfer basin at spaced locations therearound and arranged to engage the product basin to support the product basin with its side and bottom walls in spaced relation to the side and bottom walls of the heat transfer basin. The product basin is made of a size which is sufficiently small to be receivable in an autoclave of the type used in hospitals for sterilizing instruments and the basin may, for example, have a diameter of the order of 14 or 15 inches. A heat transfer medium is utilized to effect transfer of heat between the product basin and the heat transfer basin. The heat transfer medium is preferably a non-toxic fluid, for example alcohol or hospital grade glycol, having a freezing point substantially below the freezing point of the sterile liquid to be used in the production of the slush ice. The product basin is removed prior to introduction of the heat transfer medium into the heat transfer basin and the product basin is sterilized to surgical sterility as in a steam autoclave before being positioned in the product basin. A quantity of surgical sterile liquid, of a type suitable for subcutaneous administration, is introduced into the product basin after it is positioned in the heat transfer basin. The refrigeration apparatus, when operated by energization of the compressor drive motor, cools the walls of the heat transfer basin to a temperature below the freezing point of the sterile liquid, and the heat transfer medium transfers heat from the product basin to the heat transfer basin to cause congealing of the surgical sterile liquid on the walls of the product basin. A scraping tool 31, of a material which can be sterilized to surgical sterility, is provided for scraping the ice off the walls of the product basin as the sterile liquid congeals thereon, to produce a loose sterile slush ice product in the product basin. The scraping tool can be formed of metal and sterilized in a steam autoclave, but is preferably of a resilient plastic material such as polycarbonate resin which will not scratch the product basin and which can be sterilized as by gas sterilization. The loose ice tends to float upwardly in the product basin, and a quantity of the loose sterile slush ice is allowed to accumulate in the product basin. The loose sterile ice can then be removed from the product basin for immediate use in surgical procedures. The slush ice formed in this manner is of a finely divided nature and well suited for subcutaneous use in surgical procedures.

Provision is advantageously made for preventing operator contact with at least the upper portion of the cabinet during use of the apparatus, to prevent contamination of the operator. For this purpose, sterile cover means are provided for covering at least the upper portion of the cabinet outwardly of the product basin. In the preferred embodiment, the cover means includes a liquid impervious cover sheet 35 dimensioned to overlie the heat exchange basin and the top and upper portion of the cabinet. The cover sheet 35 is applied after the heat exchange medium is introduced into the heat exchange basin and overlies the cover basin and the heat exchange medium therein as well as the top of the cabinet. When the product basin is positioned in the heat transfer basin on top of the cover sheet 35, the liquid impervious cover sheet 35 is pressed into close contact with the outer walls of the product basin by the heat exchange medium and the cover sheet 35 effectively isolates the product basin from the heat exchange medium and the heat exchange basin and the upper portion of the cabinet. The liquid impervious cover sheet is preferably formed of a thin plastic sheet of a few thousandths thickness and such that it does not have a substantial adverse effect on the heat exchange between the product basin and the heat exchange medium in the heat exchange basin. The liquid impervious cover sheet 35 may conveniently be sterile plastic sheeting such as is commonly used in hospitals for surgical drapes. Such plastic surgical drapes are sealed in a sterile condition in plastic film packages and can be used as a cover for the refrigeration apparatus without requiring further sterilization.

Thin plastic sheeting such as is used for the liquid impervious cover sheet 35, can be easily punctured or torn and tends to be blown about by slight drafts or wind currents. A sterilizable outer cover sheet 36 is advantageously provided for covering the top and upper portion of the cabinet outwardly of the product basin. The outer cover sheet 36 is formed of a material which is sufficiently durable to protect the thin plastic cover sheet 35 against puncture or tearing and which is sufficiently heavy and flexible to drape along the side of the cabinet and retain the thin plastic cover sheet 35 against blowing by wind currents. The outer cover sheet is provided with an opening 36a dimensioned to allow the outer walls 25b of the product basin to pass therethrough and smaller than the rim portion 25c of the product basin so that the rim on the product basin overlies the cover sheet 36 around the opening. Thus, the outer cover sheet does not underlie the sides and bottom of the product basin, and does not interfere with heat transfer between the product basin and the heat exchange basin. The outer cover sheet need not be formed of a liquid impervious material and may for example, be formed of a cloth which can be sterilized as by gas sterilization.

From the foregoing it is thought that the method and apparatus for producing surgical sterile slush ice will be readily understood. As previously described, the refrigeration apparatus including the cabinet, heat exchange basin and refrigerating mechanism in the cabinet cannot itself be sterilized to surgical sterility, although it can be sanitized to a degree utilizing disinfectant solutions and the like. However, with the method and refrigeration apparatus disclosed, the product basin 25 is made separable from the refrigeration apparatus and of a size and material adapted to be sterilized to surgical sterility. The liquid for forming the sterilized slush ice product only contacts the inner walls of the product basin so that there is no direct contamination of the sterile liquid in the product basin or the ice produced in the product basin. The product basin is cooled by way of the heat exchange medium in the heat exchange basin. Use of the liquid impervious cover 35 to cover the heat exchange basin and the heat exchange medium therein as well as the top of the cabinet, minimizes likelihood of contamination of the product in the product basin or contamination of the operator using the apparatus. The sterilized outer cover 36 that covers the cabinet outwardly of the product basin, further reduces possibility of operator contamination by the refrigeration apparatus.

When the liquid product in the product basin congeals on the inner walls of the product basin and the sterile scraping tool 31 is used to scrape the product off the walls as it congeals thereon, to produce a loose slush ice in the product basin. After a quantity of the loose slush ice has accumulated, it can be removed from the product basin for immediate use in a surgical procedure.

The embodiments of the invention in which an exclusive property or privilege is claimed are defined as follows:

1. A method of producing surgical sterile slush ice from a surgical sterile liquid for use in surgical procedures comprising:
   (a) providing a portable refrigeration apparatus including a cabinet having an open top heat transfer basin at the top and depending side walls defining an enclosure, the refrigerating apparatus having refrigeration mechanism in the cabinet including an evaporator in heat transfer relation to the heat transfer basin and compressor means and condenser means and expansion control means connected in a closed refrigeration loop with the evaporator;
   (b) providing a separate sterilizable product basin dimensioned to be removably receivable in the heat transfer basin;
   (c) introducting a quantity of non-toxic heat transfer medium into the heat transfer basin;
   (d) sterilizing the product basin to surgical sterility and positioning the product basin in the heat transfer basin for cooling of the product basin via the heat transfer medium;
   (e) introducing a quantity of a surgical sterile liquid of a type suitable for subcutaneous administration into the product basin;
   (f) operating the refrigeration mechanism to cause congealing of the surgical sterile liquid on the walls of the product basin;
   (g) providing a sterilized scraping tool, and scraping ice off the walls of the product basin as the sterile liquid congeals thereon to produce loose sterile ice slush in the product basin; and
   (h) allowing a quantity of the loose sterile ice slush to accummulate in the product basin and removing the loose sterile ice slush from the product basin for immediate use in surgical procedures.

2. A method of producing surgical sterile slush ice according to claim 1, including providing separate sterile cover for covering at least the upper portion of the cabinet outwardly of the product basin, and positioning the sterilized cover on the upper portion of the cabinet to prevent operator contact with the upper portion of the cabinet during use of the apparatus.

3. A method of producing surgical sterile slush ice according to claim 1 including providing a separate sterile cover having an opening for receiving the product basin and adapted to cover at least the upper portion of the cabinet outwardly of the product basin, and positioning the sterile cover on the upper portion of the cabinet to prevent operator contact with the upper portion of the cabinet during use of the apparatus.

4. A method of producing a surgical sterile slush ice according to claim 1 including providing a liquid impervious cover sheet, and applying the cover sheet to cover the heat transfer basin and the upper portion of the cabinet after introduction of the heat transfer liquid into the heat transfer basin and before positioning of the product basin in the heat transfer basin.

5. A method of producing a surgical sterile slush ice according to claim 4 including providing a separate sterile cover having an opening for receiving the product basin and adapted to cover at least the upper portion of the cabinet outwardly of the product basin, and positioning the sterile cover on the upper portion of the cabinet over the liquid impervious cover sheet to prevent operator contact therewith during use of the apparatus.

6. An apparatus for producing surgical sterile slush ice from a surgical sterile liquid for use in surgical procedures comprising:
   (a) a portable refrigeration unit including a cabinet having a heat transfer basin at the top and depending side walls defining an enclosure, the refrigeration unit having a refrigeration mechanism in the cabinet including an evaporator in heat transfer relation to the heat transfer basin and compressor means and condenser means and refrigerant expansion control means connected in a closed refrigeration loop with the evaporator operable to cool the heat transfer basin to a temperature substantially below the freezing point of the sterile liquid;
   (b) a separate sterilizable product basin dimensioned to be removably receivable in the heat transfer basin, means for removably supporting the product basin in the heat transfer basin;
   (c) a heat transfer medium in the heat transfer basin for transferring heat from the product basin to the heat transfer basin;
   (d) a separate sterilized cover means removable from the cabinet for covering at least the upper portion of the cabinet outwardly of the product basin to prevent operator contact with the upper portion of the cabinet during use of the apparatus; and
   (e) means for scraping ice off the walls of the product basin as the sterile liquid product congeals thereon to produce loose sterile ice slush in the product basin.

7. An apparatus according to claim 6 wherein the sterilized cover means comprises a flexible cover member of a material capable of being sterilized to surgical sterility having an opening for receiving the product basin and adapted to extend outwardly and downwardly therefrom to cover the upper portion of the cabinet outwardly of the product basin.

8. An apparatus according to claim 6 wherein the sterilized cover means comprises a thin liquid impervious cover sheet overlying the heat transfer basin and the liquid medium therein and at least the top of the cabinet, and a flexible outer cover member of a material capable of being sterilized to surgical sterility and having an opening for receiving the product basin and adapted to extend outwardly and downwardly therefrom to cover the upper portion of the cabinet outwardly of the product basin.

* * * * *